United States Patent [19]

Flynn

[11] Patent Number: 4,584,326

[45] Date of Patent: * Apr. 22, 1986

[54] RADIOPAQUE POLYVINYL-SILICONE NETWORK RESIN COMPOSITIONS AND MEDICAL-SURGICAL TUBINGS PREPARED THEREFROM

[76] Inventor: Vincent J. Flynn, 130 New Rd., Apt. D-10, Parsippany, N.J. 07054

[ * ] Notice: The portion of the term of this patent subsequent to Apr. 1, 2003 has been disclaimed.

[21] Appl. No.: 626,149

[22] Filed: Jun. 29, 1984

[51] Int. Cl.$^4$ .......................... A01N 1/00; A61F 2/00
[52] U.S. Cl. .................................... 523/112; 523/113; 523/121; 524/288; 524/506; 524/567
[58] Field of Search ....................... 524/506, 288, 567; 523/112, 113, 121

[56] References Cited

U.S. PATENT DOCUMENTS

| | | | |
|---|---|---|---|
| 2,823,218 | 2/1958 | Speier | 260/448.2 |
| 2,970,150 | 1/1961 | Bailey | 260/348 |
| 3,159,601 | 12/1964 | Ashby | 260/46.5 |
| 3,159,622 | 12/1964 | Ashby | 260/448.2 |
| 3,361,700 | 1/1968 | Archer | 260/31.4 |
| 3,645,955 | 2/1972 | Flynn | 260/31.4 |
| 3,752,617 | 8/1973 | Burlis | 425/131 |
| 4,177,182 | 12/1979 | Ichikawa et al. | 523/112 |
| 4,211,741 | 7/1980 | Ostoich | 264/173 |
| 4,242,287 | 12/1980 | Allen | 523/112 |
| 4,250,072 | 2/1981 | Flynn | 260/31.2 N |
| 4,282,876 | 8/1981 | Flynn | 128/349 R |
| 4,283,447 | 8/1981 | Flynn | 428/36 |
| 4,451,584 | 5/1984 | Schaefer | 523/121 |

FOREIGN PATENT DOCUMENTS 961902  6/1964  United Kingdom ................ 524/288

OTHER PUBLICATIONS

Arkles & Carreno, "Silicone IPN Modified Thermoplastics", *ANTEC '84*, pp. 486–487.
Arkles, High Performance and Thermoplastic Silicones for Biomedical Applications, *ANTEC '84*, pp. 1080–1082.

*Primary Examiner*—Joseph L. Schofer
*Assistant Examiner*—N. Sarofim
*Attorney, Agent, or Firm*—Hedman, Gibson, Costigan & Hoare

[57] ABSTRACT

This invention relates to novel radiopaque resin compositions, and to medical-surgical tubings prepared therefrom. More particularly, the invention pertains to compositions of polyiodobenzoic acid ester-containing polyvinyl resins and a platinum-cured silicone network polymer dispersed therein and their use in medical-surgical devices, especially tubing and catheters.

51 Claims, 6 Drawing Figures

RADIOPAQUE POLYVINYL-SILICONE NETWORK RESIN COMPOSITIONS AND MEDICAL-SURGICAL TUBINGS PREPARED THEREFROM

This invention relates to novel radiopaque vinyl resin compositions, and medical-surgical tubings and to catheters prepared therefrom. More particularly, the invention pertains to compositions of polyiodobenzoic acid ester-containing polyvinyl resins, and a platinum-cured silicone network polymer dispersed therein and their use in medical-surgical devices, especially tubing and catheters.

CROSS-REFERENCE TO RELATED APPLICATIONS

The present application is related to the following, concurrently-filed U.S. patent applications:

| Applicant | Ser. No. | Subject Matter |
|---|---|---|
| Vincent J. Flynn | 168-005  626,209 | Radiopaque Polyvinyl-Silicone Network Resin Compositions and Medical-Surgical Tubings Prepared Therefrom |
| Vincent J. Flynn | 168-006  626,208 | Catheters Comprising Radiopaque Polyurethane-Silicone Network Resin Compositions |

BACKGROUND OF THE INVENTION

Archer and Flynn, U.S. Pat. No. 3,361,700, disclose that a family of alkoxyalkyl esters of diiodobenzoic acid are radiopaque and suitable to plasticize vinyl resins into a form useful to manufacture tubings for catheters and similar products. Flynn, U.S. Pat. No. 3,645,955 discloses that di- and tetraiodoesters used alone or in combination with the alkoxyalkyl diiodoesters are superior for this purpose because they show less tendency to exude and lower concentrations provide a better balance between flexibility and stiffness. Burlis et al., U.S. Pat. No. 3,752,617 disclose methods for making multi-wall tubing, co-tapered along its length, but make no mention of any additives, specifically by name, to produce different X-ray sensitive characteristics. Copending U.S. application Ser. No. 514,168, of Vincent J. Flynn discloses thermoplastic, e.g., polyurethane, tubing rendered non-thrombogenic with a coating layer of silicone polymer. Ostoich, U.S. Pat. No. 4,211,741 discloses a method for making a multiwall medical-surgical tubing comprising a polyvinyl chloride tubular portion and, laminated thereto via a differential-cure-temperature/rapid cooling process step, a polyurethane tubular portion.

While the iodoester opacified vinyl resin compositions of U.S. Pat. No. 3,361,700 are quite suitable for the production of tubing of simple types useful for intubation sets and catheter needles, they are not completely satisfactory for production of shaped devices. For example, if flared, or if formed into curved tips, the shapes tend to revert to straight tubing—a so-called loss of plastic memory effect. In applicant's U.S. Pat. Nos. 4,250,072 and 4,283,447, it is disclosed that such problems can be overcome if the vinyl resin is replaced partially or completely by thermoplastic polyurethane, but this tends to be expensive, especially for urethral catheters. A surface coating of silicone resin (Ser. No. 514,168) has been proposed because it helps improve ease of insertion when properly formulated, while reducing thrombogenicity, but all such constructions still can be improved, especially in terms of heat resistance and plastic memory.

More particularly, it is desirable to improve vinyl halide polymer structures in the following ways: to provide a more hydrophobic surface which allows fluid levels to be read correctly; to provide a surface with very little and, preferably, no filler exposed to minimize dangerous thrombogenic response; to provide a surface with reduced friction and wear; and to provide tubings and catheters made from such tubings which are more heat resistant and accordingly have improved sterilizability and service life.

It has now been found, and is the subject matter of the present invention, that if controlled amounts of platinum-cured silicone network polymers are employed in such compositions, tubings and catheters made therefrom will provide the above-enumerated advantages, and many others.

BRIEF DESCRIPTION OF THE DRAWINGS

The invention will be better understood by reference to the accompanying drawings in which.

DESCRIPTION OF THE INVENTION

Figure 1:
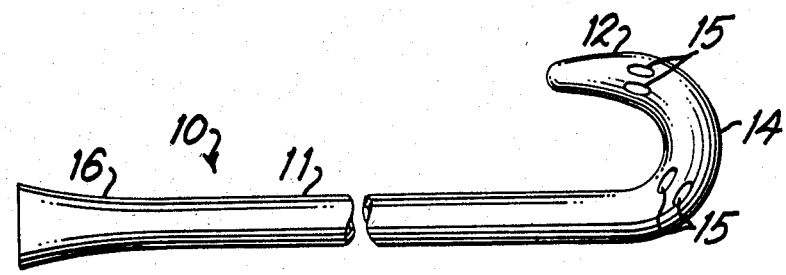
FIG. 1 is a longitudinal view of a catheter made from one form of the tubing made in accordance with the present invention and wherein, for illustrative purposes, the distal end is tapered and shaped to form a "J" tip, and the proximal end is flared.
Figure 2:
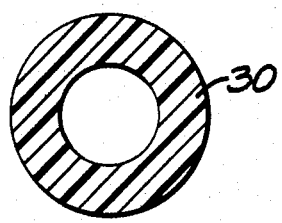
FIG. 2 is an enlarged cross-sectional view of radiopaque tubing according to this invention.
Figure 3:
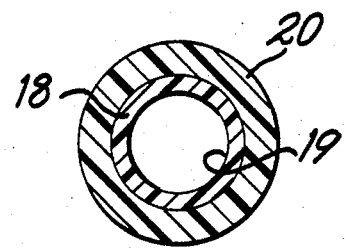
FIG. 3 is an enlarged cross-sectional view of tubing having a radiopaque inner core and a transparent outer shell.
Figure 4:
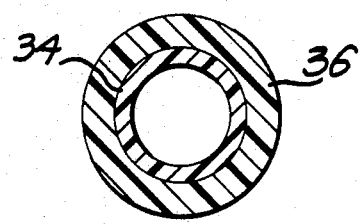
FIG. 4 is an enlarged cross-sectional view of tubing having a transparent core and a radiopaque outer shell.
Figure 5:
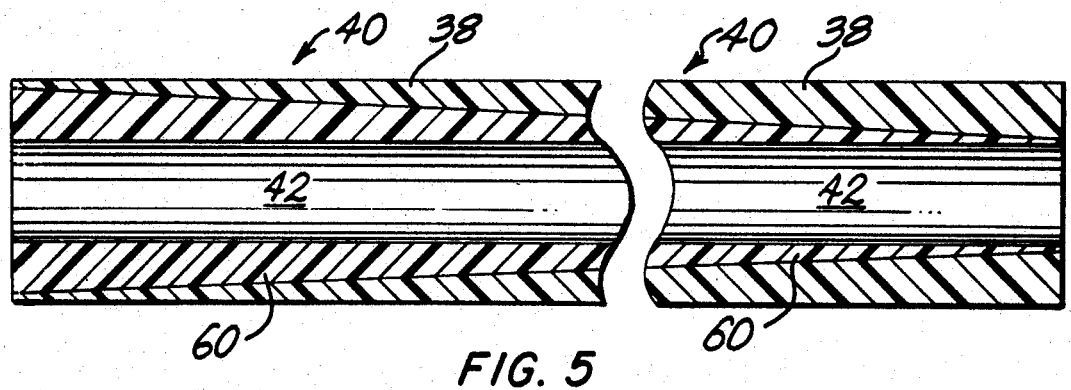
FIG. 5 is an enlarged, fragmentary cross-sectional view along the longitudinal axis of an embodiment tube of this invention having a transparent co-tapered core and a radiopaque, correspondingly co-tapered jacket, extruded as in FIG. 6.
Figure 6:
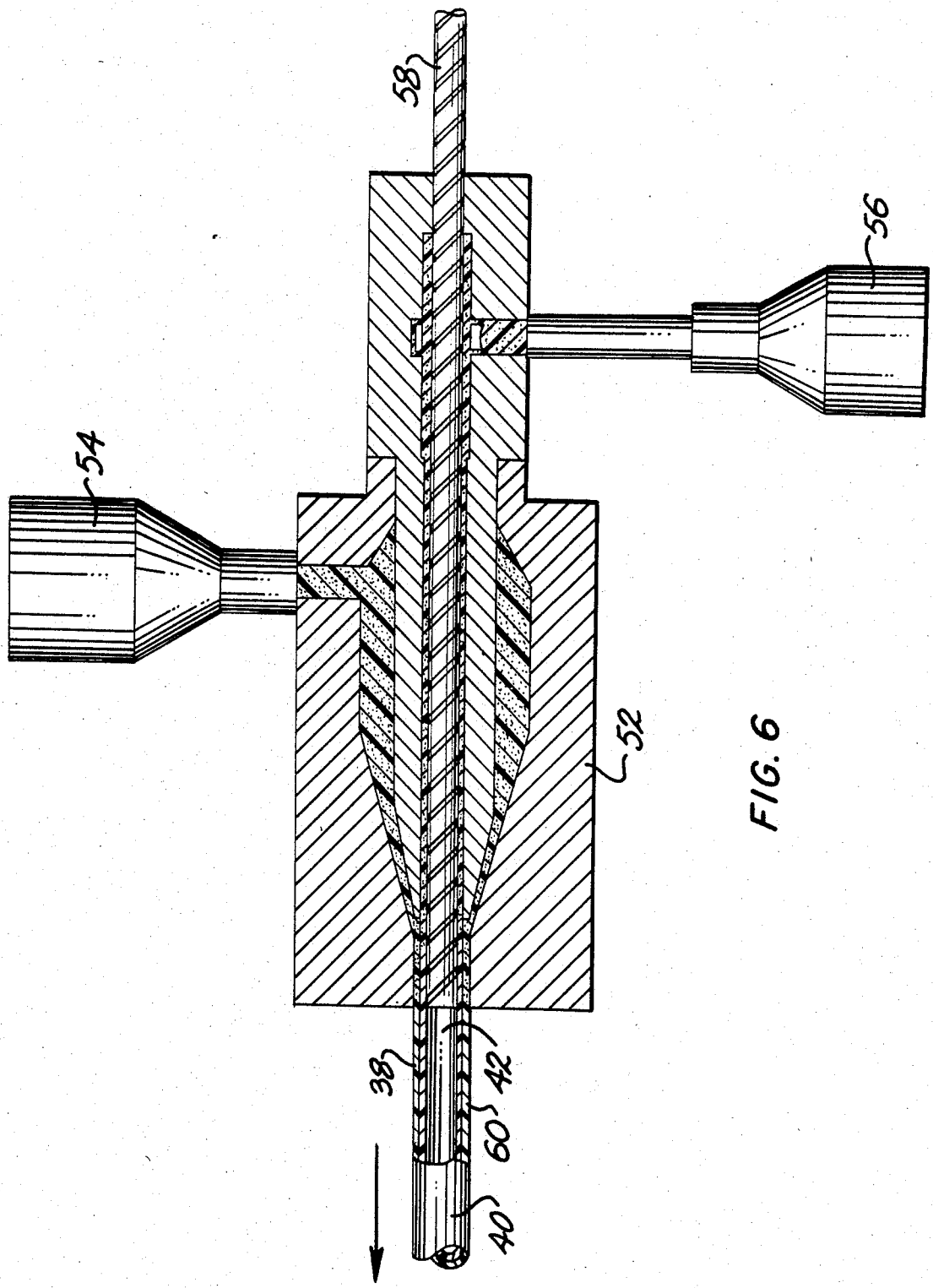

In accordance with the present invention, there are provided radiopaque compositions comprising:

(a) a vinyl resin which is a polymer or copolymer of a halogenated vinyl monomer;

(b) a radiopacifier therefor consisting of a diiodobenzoate or a tetraiodobenzoate of the formula

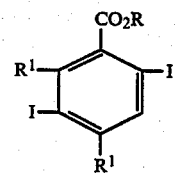

wherein $R^1$ is hydrogen or iodo, R is alkyl or alkoxyalkyl or a mixture of said compounds, said radiopacifier (b) comprising 20 to 50 parts by weight per 100 parts of (a) and (b); and, uniformly dispersed therein (c) a platinum-cured silicone network polymer, the amount of (c) comprising 2 to 30 parts by weight per 100 parts by weight of (a), (b) and (c).

The most preferred halogenated vinyl polymer will be polyvinylchloride.

Preferably, in component (b), each $R^1$ is iodo and R is (lower)alkyl or (lower)alkoxy (lower)alkyl. The most preferred radiopacifiers are n-butyl 2,3,4,6-tetraiodobenzoate, 2-ethoxyethyl 2,5-diiodobenzoate, or a mixture thereof. Optionally, there may be included in the above composition a minor amount of a radioparent plasticizer and/or a minor proportion of a heat stabilizer for the vinyl resin.

Preferably, component (c) comprises the reaction product of (i) an organic silicon compound having at least two silicon-bonded unsaturated groups per molecule, (ii) a silicon compound containing at least two silicon-bonded hydrogen atoms per molecule, and (iii) a small catalytically effective amount of a platinum-containing catalyst. Especially, preferably, the compositions will be essentially free of particulate materials, especially silica type fillers which are commonly employed with silicone polymers. The most preferred embodiments of component (c) will be those wherein (i) is of the formula:

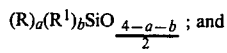; and (ii) is of the formula

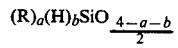

where R is selected from monovalent hydrocarbon radicals free of olefinic unsaturation, halogenated monovalent hydrocarbon radicals free of olefinic unsaturation and cyanoalkyl radicals; $R^1$ is selected from vinyl and allyl radicals; a has a value of from 1.0 to 2.5; b has a value of from 0.005 to 2.0; and the sum of a plus b is equal to from 1.005 to 3.0. In the most preferred embodiments, (iii) will be selected from chloroplatinic acid, platinum black, platinum adsorbed on a carrier, a platinum-olefin complex, a platinum-cyclopropane complex or a mixture of any of the foregoing.

In another aspect of the present invention there are provided thermocurable radiopaque compositions comprising a Part A comprised of:

(a) a vinyl resin which is a polymer or copolymer of a halogenated vinyl monomer;

(b) a radiopacifier therefor consisting of a diiodobenzoate or a tetraiodobenzoate compound of the formula:

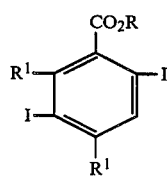

wherein $R^1$ is hydrogen or iodo, and R is alkyl or alkoxyalkyl or a mixture of said compounds, said radiopacifier comprising 20 to 50 parts by weight per 100 parts by weight of (a) and (b); and (c)(i) an organic silicon compound having at least two silicon-bonded unsaturated groups per molecule; and a Part B comprised of:

(a) a vinyl resin which is a polymer or copolymer of a halogenated vinyl monomer;

(b) a radiopacifier therefor consisting of a diiodobenzoate or a tetraiodobenzoate compound of the formula:

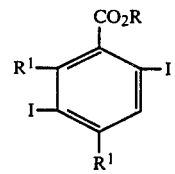

wherein $R^1$ is hydrogen or iodo, and R is alkyl or alkoxyalkyl or a mixture of said compounds, said radiopacifier comprising 20 to 50 parts by weight per 100 parts by weight of (a) and (b);

(c)(ii) a silicon compound containing at least two silicon-bonded hydrogen atoms per molecule; and (c)(iii) a small, catalytically effective amount of a platinum-containing catalyst, wherein the respective amounts of (c)(i),(ii) and (iii) are selected to provide from about 2 to about 30 parts by weight of a platinum-cured silicone network polymer, after having blended and thermo-formed parts A and B, per 100 parts by weight of the total composition. The preferred embodiments of the above thermocurable radiopaque compositions will be those wherein component (b) in part A and/or part B has as each $R^1$ an iodo and as R a (lower) alkyl or (lower)alkyl(lower)alkoxy. The most preferred embodiments will have (b), (c)(i)(ii)(iii) as previously described.

Suitable vinyl resins are described in the above-mentioned U.S. Pat. No. 3,645,955. They are available from a number of sources, such as Escambia, Nos. 3225, 3250 and 3255; Diamond No. 450 and No. 500; Borden, 106PM and Dow Chemical Co. 100-4.

The term "vinyl resin" contemplates a family of thermoplastic resinous materials consisting of polymers and copolymers of vinyl compounds. The nature of the resin is not particularly critical—so long as it is compatible with the radiopacifier (b) of the above formula and is suitable for medical use. Especially suitable are polymers and copolymers of halogenated vinyl monomers, e.g., vinyl chloride, vinylidene chloride, and vinyl esters such as polyvinyl acetate, as well as copolymers of such monomers with vinyl butyral, polyvinyl alcohol, alkyl vinyl ethers, and the like. The preferred resins will be homopolymers of vinyl chloride and copolymers of vinyl chloride with a minor proportion, e.g., from about 5 to 20 wt. percent, and especially about 10–15 wt. percent of vinyl acetate. These generally are the vinyl resins most easily compatible with the above-mentioned radiopacifier compound (b).

The radiopacifier compounds (b) can be made by procedures fully described in the above mentioned U.S. Pat. Nos. 3,645,955 and 3,361,700. In general, a 2,3,4,6-tetraiodobenzoyl halide or 2,5-diiodobenzoyl halide will be treated with an alkanol or alkoxyalkanol at ordinary temperatures, preferably in the presence of an acid acceptor. Alternatively, the free acid can be reacted with a sodium alkoxide or alkoxyalkoxide. The product can be recovered and purified in a known way, e.g., distillation.

The silicon compounds containing at least two silicon-bonded hydrogen atoms per molecule which are employed in the practice of the present invention have the formula:

$$(R)_a(H)_b SiO_{\frac{4-a-b}{2}}$$

where R is an organic radical attached to silicon through silicon-carbon linkages and free of aliphatic unsaturation. Among the organic radicals represented by R are monovalent hydrocarbon radicals free of olefinic unsaturation, halogenated monovalent hydrocarbon radicals free of olefinic unsaturation and cyanoalkyl radicals. More particularly, radicals represented by R include alkyl radicals, e.g., methyl, ethyl, propyl, butyl, octyl, etc. radicals; cycloalkyl radicals, e.g, cyclohexyl, cycloheptyl, etc. radicals; aryl radicals, e.g., phenyl, naphthyl, tolyl, xylyl, etc. radicals; aralkyl radicals, e.g, benzyl, phenylethyl, phenylpropyl, etc. radicals; halogenated radicals of the above types, including chloromethyl, chloropropyl, chlorophenyl, dibromophenyl, etc. radicals; and cyanoalkyl radicals, e.g. beta-cyanoethyl, gamma-cyanopropyl, beta-cyanopropyl, etc. radicals. Preferably, at least 50 percent of the R groups attached to silicon in the polysiloxane of the above formula are methyl radicals, with up to 50 percent of the R radicals being phenyl radicals.

The silicon compounds containing at least two silicon-bonded hydrogen atoms per molecule are well known in the art and include such materials as 1,3-dimethyldisiloxane, 1,1,3-trimethyldisiloxane, 1,1,3,3-tetramethyldisiloxane as well as higher polymers containing up to 100,000 or more silicon atoms per molecule. Also included within the scope of the above formula are cyclic materials such as the cyclic trimer or cyclic tetramer of methyl hydrogen siloxane. Such silicon compounds containing at least two silicon-bonded hydrogen atoms per molecule are described in Ashby, U.S. Pat. No. 3,159,601.

The organic silicon compounds containing at least two silicon-bonded vinyl or allyl groups per molecule which can be employed in the practice of the present invention are also well known in the art and are characterized by the formula:

$$(R)_a(R^1)_b SiO_{\frac{4-a-b}{2}}$$

where R is as previously defined and $R^1$ is a member selected from vinyl and allyl radicals.

The preparation of these vinyl- or allyl-containing silicone compounds within the scope of the above formula is well known in the art. Included within the scope of the siloxanes of the above formula are low molecular weight materials such as 1,1-divinyltetramethyldisiloxane, 1,3-divinyltetramethyldisiloxane, 1,1,3-trivinyltrimethyldisiloxane, 1,1,3,3-tetravinyldimethyldisiloxane as well as higher polymers containing up to 100,000 or more silicon atoms per molecule. Also included within the scope of the unsaturated organopolysiloxanes within the scope of the above formula are cyclic materials containing silicon-bonded vinyl or allyl radicals, such as the trimer, tetramer or pentamer, of methylvinylsiloxane or methylallylsiloxane. Such organic silicon compounds containing at least two silicon bonded vinyl or allyl groups per molecule are described as Ashby, U.S. Pat. No. b 3,159,601.

Any number of platinum-containing materials will catalyze the addition of silicon-bonded hydrogen atoms across the double bonds of compounds containing olefinic unsaturation. For example, Bailey, U.S. Pat. No. 2,970,150, shows the use of a platinum-on-charcoal catalysts, Speier, et al., U.S. Pat. No. 2,823,218, show the use of chloroplatinic acid, and Ashby, U.S. Pat. No. 3,159,622, shows the use of a platinum-cyclopropane complex. These and many other platinum-containing catalysts may be employed in the practice of the present invention. Preferred platinum-containing catalysts will be those described in Ashby, U.S. Pat. No. 3,159,601, which describes platinum-olefin complexes having the formulae:

(1) $[PtCl_2.Olefin]_2$
(2) $H[PtCl_3.Olefin]$ wherein the olefin portion of (1) and (2) may be any olefin, but is preferably an alkene having from 2 to 8 carbon atoms, a cycloalkene having from 5 to 7 carbon atoms, or styrene.

When used in the appended claims, the term "alkyl" contemplates straight and branched chain radicals of from 1 to 30 carbon atoms, and the term "(lower)alkyl" contemplates such groups of from 1 to 6 carbon atoms.

In preparing the compositions, according to techniques known to those skilled in the art, various additional ingredients such as plasticizers, stabilizers, lubricants, fillers, pigments and the like may be added to secure advantages desired and expected in any vinyl resin formulation.

In embodiments of this invention, for example, compositions and medical-surgical tubing prepared therefrom will include a minor proportion, e.g., from 1 to 20% by weight, of a radioparent, i.e., conventional, X-ray transparent, plasticizer and a minor proportion, e.g., from 0.5 to 5% by weight, of a heat stabilizer, both based on weight of total composition.

The radioparent, conventional plasticizer will be employed to impart flexibility, often more economically than can be achieved with the polyiodo compounds alone. Suitable radioparent plasticizers are high boiling liquid esters, for example, dialkyl esters of aromatic and aliphatic polybasic acids, such as phthalates, adipates, sebacates and azelates, e.g., dioctyl phthalate, dioctyl adipate, di-2-ethylhexyl azelate, dibutyl sebacate and the like. These are all commercially available. For example, dioctyl adipate is available from Rohm and Haas Company under the name Monoplex DIOA.

Epoxy plasticizers too are very useful as radioparent plasticizers since they also help to stabilize the resin. Epoxidized soy bean oil, epoxidized triglycerides and the like are illustrative.

One such epoxy plasticizer is Epoxol 9-5, commercially available from Swift Chemical Company. It is an epoxidized triglyceride with good resistance to heat and light and has a minimum 9% oxirane content. The specific gravity at 25° C. is 1.020 and the flash point is 320° C.

Heat stabilizers for vinyl resins are well known to those skilled in the art. These are metallic salts—some solid, some liquid—based on tin, calcium and zinc. Epoxy plasticizers are often used with them for a synergistic effect. For medical use, calcium and zinc in limited amounts are preferred for their low toxicity, and can be used with epoxide.

One such calcium zinc stabilizer is a fluid paste containing non-toxic compounds of calcium and zinc. It is white and is insoluble in most common solvents and plasticizers. It is commercially available from Advance Division of Carlisle Chemical Works, Inc., under designation CZ-11C.

The formulations will be aided in some cases by the inclusion of lubricants such as metallic stearate, stearic acid, paraffin wax, mineral oil, etc., in conventional amounts. See U.S. Pat. No. 3,645,955, incorporated herein to minimize unnecessarily detailed description.

The compositions are prepared and converted into useful products by techniques well known to those skilled in the art.

In one manner of proceeding, the fluid ingredients, e.g., radiopaque compound(s) if liquid, are blended with the powdered solids, e.g., thermoplastic polyvinyl resin, reactive curable silicone components, and, optionally, stabilizers and plasticizers, and then fused and mixed under pressure, e.g., in a Banbury-type mixer and discharged. Conventional 2-roll compounding techniques can also be used. The composition is cooled and granulated.

If extrusions are to be made, the granulated composition can be fed to a conventional machine, for example, a 30 millimeter Reifenhouser-type single screw extruder operated at suitable temperature, e.g., 280°–330° F. and the tubing or other shapes formed at a suitable rate, e.g., 7,000–10,000 feet per hour and cut automatically to length.

In another manner of proceeding, a thermocurable radiopaque composition comprising a part A and a part B, previously described, may be prepared and extruded, with or without precompounding either A and B, as mentioned above. Optionally, A and B will be precompounded and thereafter extruded under suitable conditions.

In still another manner of proceeding, multiwall tubing, of uniform or co-tapered wall construction, may be prepared by co-extruding a thermocurable radiopaque composition, comprising a part A and a part B, with another thermoplastic resin, or with another, differently formulated, thermocurable radiopaque composition comprising a part A and a part B.

In still another manner of proceeding, multiwall tubing may be prepared by co-extruding a thermocurable composition, comprising a part A and a part B, with a thermoplastic polyurethane outer shell. The thermoplastic polyurethanes suitable for this aspect of the present invention are known to those skilled in this art. They are described in the Encyclopedia of Polymer Science and Technology, Vol. 11, pages 506–563, New York, Interscience Publishers, 1969, and especially on page 549. The are also commercially available from a number of suppliers, such as Hooker, as Rucothenes, especially 3713, and from Upjohn, as Pellethene, e.g., 75D, 85D and X-010155 80D, and from Mobay, as Texin.

Those skilled in the art will prepare a variety of thermocurable compositions comprising A and B wherein components (c)(i),(ii) and (iii), previously described, may be varied to effect different cure rates, degrees of cross-linking and/or physical/chemical properties of the finished compositions.

As is pointed out above, the compositions of this invention can be used for many various and diverse purposes, e.g., protective sheeting, surgeon's gloves, intubation sets, heart catheters, stomach tubes, nasal tubes, thoracic catheters and the like. The following examples primarily illustrate the use of these compositions in the form of single and multiple wall surgical tubing. However, from the foregoing description and the following examples and by reference to other well known teachings, the methods and modes by which are plasticized radiopaque vinyl resin compositions of this invention can be formed into various other articles will be readily apparent to those skilled in the art.

The medical grade radiopaque tubing prepared as described in the following examples is non-toxic, non-reactive to tissue and may be sterilized by gas, cold sterilization solutions or heat sterilization techniques. The tubing is generally dispensed as such and the surgeon or trained technician will form it into catheters for roentgenography. For maximum convenience, the tubing can also be preformed into articles and dispensed, e.g., as sterile disposable intravenous catheters.

By way of illustration, catheters according to this invention will be fabricated from the medical-surgical tubing of the following examples by operations comprising tip forming, tip finishing, shaping, side hole forming, and flaring. Before use they will be sterilized.

Those skilled in the art will prepare a variety of tip shapes. For internal mammary and axillary artery branches a three-quarter loop is formed in the distal end. For precutaneous arteriography and cerebral arteriography via femoral, a 45°–60° smooth bend will be formed in the distal end. Selective renal arteriography and celiac arteriography requires a one-half loop. Hepatic venography uses about a seven-eighths loop. For trans-septal left-heart catheterization via the femoral vein, a three-quarter loop, like that above-described for mammary branches, but larger, is formed. On the other hand, abdominal aortography via brachial artery uses a rather large, one-third closed loop and thoracic aortography via the femoral artery uses the same shape but bigger. For lumbar aortography via the femoral artery the tip is straight out. For coronary arteriography, the end of the catheter is looped.

The heavier-walled tubing is formed into such typical shapes by inserting a forming wire within the tubing and heating in a tiny flame until visibly softened. By pulling from both ends the tubing is drawn to the wire and forms a uniform lumen around it. The tip is formed by cutting, e.g., with a razor blade, at the drawn diameter and is smoothly rounded in the flame. Next a precurved wire is inserted into the tube which is then immersed in hot water until the tubing softens. Quenching in cold water will cause the catheter to conform to the curve of the forming wire. Side hole or eye punching is accomplished by rotating a sharpened hole punch cannula under slight pressure. The holes should be large enough to expel contrast media without excess build up of injection pressures but should be no larger than ⅝ of the internal diameter of the tubing. The catheter is cut to the preselected length and flared. Heating in a small flame and rotating on a flaring tool produces a flare of the desired size. The catheter can be bonded at the flare, e.g., with epoxy cement, to a suitable hub. On the other hand, an adapter can be used to screw the catheter to a Leur-Lok stopcock, or the like.

DESCRIPTION OF THE PREFERRED EMBODIMENTS

The following non-limiting examples illustrate the present invention.

EXAMPLE 1

(Silicone network polymer-20%)

| PART A | |
|---|---|
| Composition (parts by weight) | |
| Resin, thermoplastic polyvinylchloride, BK 80[a] | 1800 |
| 2-Ethoxyethyl-2,5-diiodobenzoate | 600 |
| n-Butyl 2,3,4,6-tetraiodobenzoate | 600 |
| Plasticizer, Epoxol 9-5[b] | 160 |
| Heat stabilizer, CZ-11C[c] | 40 |
| Methylvinyl polysiloxane[d] | 800 |
| PART B | |
| Composition (parts by weight) | |
| Resin, thermoplastic polyvinylchloride, BK 80 | 1800 |
| 2-Ethoxyethyl-2,5-diiodobenzoate | 600 |
| n-Butyl 2,3,4,6-tetraiodobenzoate | 600 |
| Plasticizer, Epoxol 9-5[b] | 160 |
| Heat stabilizer, CZ-11C[c] | 40 |
| Methylhydrogen polysiloxane[e] | 800 |
| Platinum-olefin complex catalyst[f] | 0.080 |

[a] Goodyear Corp.
[b] Advance Division of Carlisle Chemical Works.
[c] Swift & Co.
[d] e.g., Methylvinylpolysiloxane fluid, 200 cps @ 25° C. comprising trimethylsilyl chain-stopping units and consisting of 2.0 mole percent methylvinylsiloxane units with the remainder of the diorganosiloxane units being dimethylsiloxane units. Example 8, U.S. Pat. No. 3,159,601.
[e] e.g., Methylhydrogenpolysiloxane fluid, 200 cps @ 25° C., comprising trimethylsilyl chainstopping units and consisting of 2.0 mole percent methylhydrogensiloxane units with the remainder of the diorganosiloxane units being dimethylsiloxane units. Example 8, U.S. Pat. No. 3,159,601.
[f] (Pt Cl$_2$·C$_2$H$_4$)$_2$ Example 2, U.S. Pat. No. 3,159,601.

The fluids are mixed in a planetary mixer, e.g., a Hobart mixer, for 15 minutes. The powdered ingredients are added and mixed for 1.5 hours. The mixture is fluxed and mixed in a Banbury—one 10–15 min. cycle—and discharged. The partially cooled mass is granulated through ⅛ in. or ¼ in. screen. The granulated product is extruded in a 30 mm. Reinfenhauser single screw extruder at 280°–330° F. at 7,000–10,000 feet per hour into medical-surgical tubing, 0.065 O.D.×0.046 I.D.—wall 0.010 exceeding minimum specifications of tensile break strength, elongation and flexural strength for use as intubation sets and in catheter needles.

EXAMPLE 2

The general procedure of Example 1 is repeated, substituting the formulation below, and a medium hard tubing according to this invention is obtained.

| PART A | |
|---|---|
| (Silicone network polymer - 10%) | |
| Composition (parts by weight) | |
| Resin, thermoplastic polyvinylchloride, BK 80[a] | 1800 |
| 2-Ethoxyethyl-2,5-diiodobenzoate | 491 |
| n-Butyl 2,3,4,6-tetraiodobenzoate | 491 |
| Plasticizer, Epoxol 9-5[b] | 131 |
| Heat stabilizer, CZ-11C[c] | 33 |
| Methylvinyl polysiloxane[d] | 327 |
| PART B | |
| Composition (parts by weight) | |
| Resin, thermoplastic polyvinylchloride, BK 80 | 1800 |
| 2-Ethoxyethyl-2,5-diiodobenzoate | 491 |
| n-Butyl 2,3,4,6-tetraiodobenzoate | 491 |
| Plasticizer, Epoxol 9-5[b] | 131 |
| Heat stabilizer, CZ-11C[c] | 33 |
| Methylhydrogen polysiloxane[e] | 327 |
| Platinum-olefin complex catalyst[f] | 0.03 |

[a]–[f] See Example 1, footnotes [a]–[f].

EXAMPLE 3

The general procedure of Example 1 is repeated, substituting the formulation below, and a soft tubing according to this invention is obtained.

| PART A | |
|---|---|
| (Silicone network polymer - 20%) | |
| Composition (parts by weight) | |
| Resin, thermoplastic polyvinylchloride, BK 80[a] | 1800 |
| 2-Ethoxyethyl-2,5-diiodobenzoate | 1200 |
| n-Butyl 2,3,4,6-tetraiodobenzoate | — |
| Plasticizer, Epoxol 9-5[b] | 160 |
| Heat stabilizer, CZ-11C[c] | 40 |
| Methylvinyl polysiloxane[d] | 800 |
| PART B | |
| Composition (parts by weight) | |
| Resin, thermoplastic polyvinylchloride, BK 80 | 1800 |
| 2-Ethoxyethyl-2,5-diiodobenzoate | 1200 |
| n-Butyl 2,3,4,6-tetraiodobenzoate | — |
| Plasticizer, Epoxol 9-5[b] | 160 |
| Heat stabilizer, CZ-11C[c] | 40 |
| Methylhydrogen polysiloxane[e] | 800 |
| Platinum-olefin complex catalyst[f] | 0.08 |

[a]–[f] See Example 1, footnotes [a]–[f].

EXAMPLE 4

The general procedure of Example 1 is repeated, substituting the formulation below, and a hard tubing according to this invention is obtained.

| PART A | |
|---|---|
| (Silicone network polymer - 5%) | |
| Composition (parts by weight) | |
| Resin, thermoplastic polyvinylchloride, BK 80[a] | 1800 |
| 2-Ethoxyethyl-2,5-diiodobenzoate | 600 |
| n-Butyl 2,3,4,6-tetraiodobenzoate | 300 |
| Plasticizer, Epoxol 9-5[b] | 120 |
| Heat stabilizer, CZ-11C[c] | 30 |
| Methylvinyl polysiloxane[d] | 150 |
| PART B | |
| Composition (parts by weight) | |
| Resin, thermoplastic polyvinylchloride, BK 80 | 1800 |
| 2-Ethoxyethyl-2,5-diiodobenzoate | 600 |
| n-Butyl 2,3,4,6-tetraiodobenzoate | 300 |
| Plasticizer, Epoxol 9-5[b] | 120 |
| Heat stabilizer, CZ-11C[c] | 30 |
| Methylhydrogen polysiloxane[e] | 150 |
| Platinum-olefin complex catalyst[f] | 0.015 |

[a]–[f] See Example 1, footnotes [a]–[f].

EXAMPLE 5

The general procedure of Example 1 is repeated, substituting the formulation below, and a medium hard tubing according to this invention is obtained.

| PART A | |
|---|---|
| (Silicone network polymer - 12%) | |
| Composition (parts by weight) | |
| Resin, thermoplastic polyvinylchloride, No. 3225[a] | 1800 |
| 2-Ethoxyethyl-2,5-diiodobenzoate | — |
| n-Butyl 2,3,4,6-tetraiodobenzoate | 1275 |
| Plasticizer, Epoxol 9-5[b] | 188 |
| Heat stabilizer, CZ-11C[c] | 38 |
| Methylvinyl polysiloxane[d] | 450 |

-continued

| PART B | |
|---|---|
| Composition (parts by weight) | |
| Resin, thermoplastic polyvinylchloride, No. 3255 | 1800 |
| 2-Ethoxyethyl-2,5-diiodobenzoate | — |
| n-Butyl 2,3,4,6-tetraiodobenzoate | 1275 |
| Plasticizer, Epoxol 9-5[b] | 188 |
| Heat stabilizer, CZ-11C[c] | 38 |
| Methylhydrogen polysiloxane[e] | 450 |
| Platinum-olefin complex catalyst[f] | 0.045 |

[a]Escambia Corp.
[b-f]See Example 1, footnotes [b-f].

EXAMPLE 6

A multi-wall radiopaque vinyl medical-surgical tubing of 0.110 inch outer diameter and 0.071 inch inner diameter is extruded in a conventional manner employing a bi-orifice tubular die for co-extrusion of two concentric bonded tubings wherein the inner tube has a thickness of 0.0175 inch and the outer shell has a thickness of 0.002 inch.

| Inner Core (Silicone network polymer - 18%) | |
|---|---|
| PART A | |
| Composition (parts by weight) | |
| Resin, thermoplastic polyvinylchloride, 100-4[a] | 1800 |
| 2-Ethoxyethyl-2,5-diiodobenzoate | — |
| n-Butyl 2,3,4,6-tetraiodobenzoate | 1350 |
| Radioparent plasticizer, Monoplex DIOA[b] | 360 |
| Plasticizer, Epoxol 9-5[c] | 144 |
| Heat stabilizer, CZ-11C[d] | 36 |
| Methylvinyl polysiloxane[e] | 810 |
| PART B | |
| Composition (parts by weight) | |
| Resin, thermoplastic polyvinylchloride, 100-4 | 1800 |
| 2-Ethoxyethyl-2,5-diiodobenzoate | — |
| n-Butyl 2,3,4,6-tetraiodobenzoate | 1350 |
| Radioparent plasticizer, Monoplex DIOA | 360 |
| Plasticizer, Epoxol 9-5 | 144 |
| Heat stabilizer, CZ-11C[c] | 36 |
| Methylhydrogen polysiloxane[f] | 810 |
| Platinum-olefin complex catalyst[g] | 0.081 |
| Outer Shell (Silicone network polymer - 12.5%) | |
| PART A | |
| Composition (parts by weight) | |
| Resin, thermoplastic polyvinylchloride, 100-4[a] | 1800 |
| 2-Ethoxyethyl-2,5-diiodobenzoate | — |
| n-Butyl 2,3,4,6-tetraiodobenzoate | 2520 |
| Radioparent plasticizer, Monoplex DIOA[b] | — |
| Plasticizer, Epoxol 9-5[c] | 144 |
| Heat stabilizer, CZ-11C[d] | 36 |
| Methylvinyl polysiloxane[e] | 643 |
| PART B | |
| Composition (parts by weight) | |
| Resin, thermoplastic polyvinylchloride, 100-4 | 1800 |
| 2-Ethoxyethyl-2,5-diiodobenzoate | — |
| n-Butyl 2,3,4,6-tetraiodobenzoate | 2520 |
| Radioparent plasticizer, Monoplex DIOA | — |
| Plasticizer, Epoxol 9-5 | 144 |
| Heat stabilizer, CZ-11C[c] | 36 |
| Methylhydrogen polysiloxane[f] | 643 |
| Platinum-olefin complex catalyst[g] | 0.064 |

[a]Dow Chemical co.
[b]Rohm and Haas Co.
[c-g]See Example 1, footnotes [b-f].

This vinyl multi-wall medical-surgical tubing is found to have the described desired properties necessary for medical-surgical tubing.

EXAMPLE 7

A multi-wall radiopaque vinyl medical-surgical tubing particularly useful for thoracic, stomach and nasal use having an outer diameter of 0.348 inch and an inner diameter of 0.25 inch is extruded in a conventional manner employing a bi-orifice tubular die for co-extrusion of two concentric bonded tubings wherein the inner tube has a thickness of 0.039 inch and the outer jacket has a thickness of 0.0085 inch.

| Inner Core (Silicone network polymer - 10%) | |
|---|---|
| PART A | |
| Composition (parts by weight) | |
| Resin, thermoplastic polyvinylchloride, 100-4[a] | 1800 |
| Radioparent plasticizer, dioctyl phthalate | 1188 |
| Plasticizer, Epoxol 9-5[b] | 540 |
| Heat stabilizer, CZ-11C[c] | 72 |
| Methylvinyl polysiloxane[d] | 400 |
| PART B | |
| Composition (parts by weight) | |
| Resin, thermoplastic polyvinylchloride, 100-4 | 1800 |
| Radioparent plasticizer, dioctyl phthalate | 1188 |
| Plasticizer, Epoxol 9-5 | 540 |
| Heat stabilizer, CZ-11C[c] | 72 |
| Methylhydrogen polysiloxane[f] | 400 |
| Platinum-olefin complex catalyst[g] | 0.040 |
| Outer Shell (Silicone network polymer - 10%) | |
| PART A | |
| Composition (parts by weight) | |
| Resin, thermoplastic polyvinylchloride, 100-4[a] | 1800 |
| 2-Ethoxyethyl-2,5-diiodobenzoate | 1260 |
| Plasticizer, Epoxol 9-5[b] | 162 |
| Heat stabilizer, CZ-11C[c] | 32 |
| Methylvinyl polysiloxane[d] | 360 |
| PART B | |
| Composition (parts by weight) | |
| Resin, thermoplastic polyvinylchloride, 100-4 | 1800 |
| 2-Ethoxyethyl-2,5-diiodobenzoate | 1260 |
| Plasticizer, Epoxol 9-5 | 162 |
| Heat stabilizer, CZ-11C | 32 |
| Methylhydrogen polysiloxane[e] | 360 |
| Platinum-olefin complex catalyst[f] | 0.036 |

[a]Dow Chemical co.
[b-f]See Example 1, footnotes [b-f].

This multi-wall medical-surgical tubing has a slick, glass-like surface. It is pale rose tan and clear. Radiopacity is excellent. The composition and tubing are useful in this size for thoracic catheters.

EXAMPLE 8

A multi-wall radiopaque vinyl medical-surgical tubing according to this invention is extruded in a conventional manner employing a bi-orifice tubular die for co-extrusion of two concentric bonded tubings wherein the inner tubular portion is of a radiopaque polyvinyl chloride/silicone network polymer composition and wherein the outer shell is a clear polyurethane.

| Inner Core (Silicone network polymer - 20%) | |
|---|---|
| PART A | |
| Composition (parts by weight) | |
| Resin, thermoplastic polyvinylchloride, BK 80[a] | 1800 |
| 2-Ethoxyethyl-2,5-diiodobenzoate | 600 |
| n-Butyl 2,3,4,6-tetraiodobenzoate | 600 |
| Plasticizer, Epoxol 9-5[b] | 160 |
| Heat stabilizer, CZ-11C[c] | 40 |
| Methylvinyl polysiloxane[d] | 800 |
| PART B | |
| Composition (parts by weight) | |
| Resin, thermoplastic polyvinylchloride, BK 80 | 1800 |
| 2-Ethoxyethyl-2,5-diiodobenzoate | 600 |
| n-Butyl 2,3,4,6-tetraiodobenzoate | 600 |
| Plasticizer, Epoxol 9-5 | 160 |
| Heat stabilizer, CZ-11C | 40 |
| Methylhydrogen polysiloxane[e] | 800 |
| Platinum-olefin complex catalyst[f] | 0.080 |

-continued

| Outer Shell | |
|---|---|
| Composition (parts by weight) | |
| Resin, thermoplastic polyurethane, (Pellethane 75-80 D)[g] | 1800 |

[a-f]See Example 1, footnotes [a-f].
[g]Upjohn Co.

The foregoing patents and publications are incorporated herein by reference. Obviously, many variations will suggest themselves to those skilled in this art in light of the above, detailed description. All such obvious variations are within the full intended scope of the appended claims.

What is claimed is:

1. A radiopaque composition comprising:
   (a) a vinyl resin which is a polymer or copolymer of a halogenated vinyl monomer;
   (b) a radiopacifier therefor consisting of a diiodobenzoate or a tetraiodobenzoate compound of the formula:

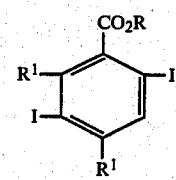

wherein
   $R^1$ is hydrogen or iodo;
   R is alkyl or alkoxyalkyl or a mixture of said compounds, said radiopacifier comprising 20 to 50 parts by weight per 100 parts by weight of (a) and (b); and, uniformly dispersed therein,
   (c) a platinum-cured silicone network polymer, the amount of (c) comprising 2 to 30 parts by weight per 100 parts by weight of (a), (b) and (c), wherein said radiopaque composition is essentially free of filler.

2. A composition according to claim 1 which includes a minor proportion of a radioparent plasticizer and a minor proportion of a heat stabilizer for said vinyl resin.

3. A composition according to claim 1 wherein, in said radiopacifier (b), each $R^1$ is iodo and R is (lower)alkyl or (lower)alkoxy(lower)alkyl.

4. A composition according to claim 1 wherein said radiopacifier (b) is n-butyl 2,3,4,6-tetraiodobenzoate.

5. A composition according to claim 1 wherein said radiopacifier (b) is 2-ethoxyethyl 2,5-diiodobenzoate.

6. A composition according to claim 1 wherein said radiopacifier (b) comprises a mixture of n-butyl 2,3,4,6-tetraiodobenzoate and 2-ethoxyethyl 2,5-diiodobenzoate.

7. A composition as defined in claim 1 which is essentially free of particulate silica.

8. A composition as defined in claim 1 wherein said platinum-cured silicone network polymer (c) comprises the reaction product of
   (i) an organic silicon compound having at least two silicon-bonded unsaturated groups per molecule,
   (ii) a silicon compound containing at least two silicon-bonded hydrogen atoms per molecule, and
   (iii) a small, catalytically effective amount of a platinum-containing catalyst.

9. A composition as defined in claim 8 wherein component (i) is of the formula:

$$(R)_a(R^1)_b SiO_{\frac{4-a-b}{2}};$$

and component (ii) is of the formula:

$$(R)_a(H)_b SiO_{\frac{4-a-b}{2}}$$

wherein R is selected from monovalent hydrocarbon radicals free of olefinic unsaturation, halogenated monovalent hydrocarbon radicals free of olefinic unsaturation, cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

10. A composition as defined in claim 9 wherein said platinum-containing catalyst (iii) is selected from chloroplatinic acid, platinum-black, platinum adsorbed on a carrier, a platinum-olefin complex, a platinum-cyclopropane complex or a mixture of any of the foregoing.

11. A two-part composition adapted for melt blending and thermoforming into radiopaque tubing,
   Part A comprising:
   (a) a vinyl resin which is a polymer or copolymer of a halogenated vinyl monomer;
   (b) a radiopacifier therefor consisting of a diiodobenzoate or a tetraiodobenzoate compound of the formula:

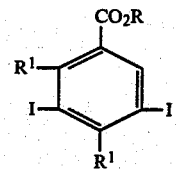

wherein $R^1$ is hydrogen or iodo, and R is alkyl or alkoxyalkyl or a mixture of said compounds, said radiopacifier comprising 20 to 50 parts by weight per 100 parts by weight of (a) and (b); and
   (c)(i) an organic silicon compound having at least two silicon-bonded unsaturated groups per molecule; and
   Part B comprising:
   (a) a vinyl resin which is a polymer or copolymer of a halogenated vinyl monomer;
   (b) a radiopacifier therefor consisting of a diiodobenzoate or a tetraiodobenzoate compound of the formula:

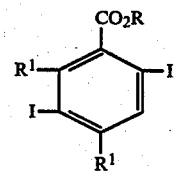

wherein $R^1$ is hydrogen or iodo, and R is alkyl or alkoxyalkyl or a mixture of said compounds, said radiopacifier comprising 20 to 50 parts by weight per 100 parts by weight of (a) and (b);
   (c)(ii) a silicon compound containing at least two silicon-bonded hydrogen atoms per molecule; and (c)(iii) a small, catalytically effective amount of a platinum-containing catalyst, wherein the respective amounts of (c)(i), (ii) and (iii) are selected to provide from about 2 to about 30 parts by weight of a platinum-cured silicone network polymer, after having blended and thermoformed parts A and B, per 100 parts by weight of the total composition, and wherein said two-part composition is essentially free of filler.

12. A two-part composition as defined in claim 11 wherein in said radiopacifier (b), each $R^1$ is iodo and R is (lower)alkyl or (lower)alkoxy(lower)alkyl.

13. A two-part composition as defined in claim 11 wherein said radiopacifier (b) is selected from n-butyl 2,3,4,6-tetraidobenzoate, 2-ethoxyethyl 2,5-diiodobenzoate or a mixture of the foregoing.

14. A two-part composition as defined in claim 11 which is essentially free of particulate silica.

15. A two part composition as defined in claim 11 wherein component (c)(i) of Part A is of the formula:

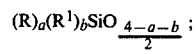

and component (c)(ii) of Part B is of the formula:

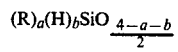

where R is selected from monovalent hydrocarbon radicals free of olefinic unsaturation, halogenated monovalent hydrocarbon radicals free of olefinic unsaturation and cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

16. A two-part composition as defined in claim 15 wherein component (c)(iii) is selected from chloroplatinic acid, platinum black, platinum adsorbed on a carrier, a platinum-olefin complex, a platinum-cyclopropane complex or a mixture of any of the foregoing.

17. Medical-surgical tubing comprising:
(a) a vinyl resin which is a polymer or copolymer of a halogenated vinyl monomer;
(b) a radiopacifier therefor consisting of a diiodobenzoate or a tetraiodobenzoate compound of the formula:

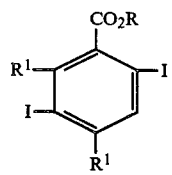

wherein $R^1$ is hydrogen or iodo, and R is alkyl or alkoxyalkyl or a mixture of said compounds, said radiopacifier (b) comprising 20 to 50 parts by weight per 100 parts by weight of (a) and (b); and, uniformly dispersed therein,
(c) a platinum-cured silicone network polymer, the amount of (c) comprising 8 to 30 parts by weight per 100 parts by weight of (a), (b) and (c), wherein said medical-surgical tubing is essentially free of filler.

18. Medical-surgical tubing according to claim 17 which includes a minor proportion of a radioparent plasticizer and a minor proportion of a heat stabilizer for said vinyl resin.

19. Medical-surgical tubing as defined in claim 17 wherein, in said radiopacifier (b), each $R^1$ is iodo and R is (lower)alkyl or (lower)alkoxy(lower)alkyl.

20. Medical-surgical tubing as defined in claim 17 wherein said radiopacifier (b) is n-butyl 2,3,4,6-tetraiodobenzoate.

21. Medical-surgical tubing as defined in claim 17 wherein said radiopacifier (b) is 2-ethoxyethyl 2,5-diiodobenzoate.

22. Medical-surgical tubing as defined in claim 17 wherein said radiopacifier (b) is a mixture of n-butyl 2,3,4,6-tetraiodobenzoate and 2-ethoxyethyl 2,5-diiodobenzoate.

23. Medical-surgical tubing as defined in claim 17 which also includes as a partial replacement for said radiopacifier (b) a compound selected from bismuth oxychloride or barium sulfate in an amount sufficient to enhance the radiopacity of said tubing while maintaining its tensile strength.

24. Medical-surgical tubing as defined in claim 17 which is essentially free of particulate silica.

25. Medical-surgical tubing as defined in claim 17 wherein said platinum-cured silicone network polymer (c) comprises the reaction product of:
(i) an organic silicon compound having at least two silicon-bonded unsaturated groups per molecule,
(ii) a silicon compound containing at least two silicon-bonded hydrogen atoms per molecule, and
(iii) a small, catalytically effective amount of a platinum-containing catalyst.

26. Medical-surgical tubing as defined in claim 25 wherein component (i) is of the formula:

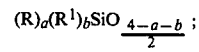

and component (ii) is of the formula:

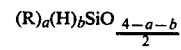

where R is selected from monovalent hydrocarbon radicals free of olefinic unsaturation, halogenated monovalent hydrocarbon radicals free of olefinic unsaturation and cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

27. Medical-surgical tubing as defined in claim 26 wherein component (iii) is selected from chloroplatinic acid, platinum black, platinum adsorbed on a carrier, a platinum-olefin complex, platinum-cyclopropane complex or a mixture of any of the foregoing.

28. A medical-surgical catheter formed from the tubing of claim 17.

29. A medical-surgical tubing comprising:
(1) an interior tubular portion comprising:
(a) a vinyl resin which is a polymer or copolymer of a halogenated vinyl monomer; and
(2) a concentric outer shell comprising:
(a) a vinyl resin which is a polymer or copolymer (b) a radiopacifier therefor consisting of a diiodobenzoate or a tetraiodobenzoate compound of the formula:

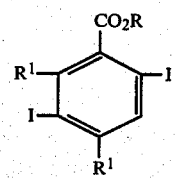

wherein $R^1$ is hydrogen or iodo, and R is alkyl or alkoxyalkyl or a mixture of said compounds, said radiopacifier (b) comprising 20 to 50 parts by weight per 100 parts by weight of (a) and (b); and, uniformly dispersed therein, (c) a platinum-cured, silicone network polymer, the amount of (c) comprising 2 to 30 parts by weight per 100 parts by weight of (a), (b) and (c), wherein said medical-surgical tubing is essentially free of filler.

30. A medical-surgical tubing as defined in claim 29 wherein, in said radiopacifier (b), each $R^1$ is iodo and R is (lower)alkyl or (lower)alkoxy(lower)alkyl.

31. A medical-surgical tubing as defined in claim 29 wherein said radiopacifier (b) is n-butyl 2,3,4,6-tetraiodobenzoate.

32. A medical-surgical tubing as defined in claim 29 wherein said radiopacifier (b) is 2-ethoxyethyl 2,5-diiodobenzoate.

33. A medical-surgical tubing as defined in claim 29 wherein said radiopacifier (b) comprises a mixture of n-butyl 2,3,4,6-tetraiodobenzoate and 2-ethoxyethyl 2,5-diiodobenzoate.

34. A medical-surgical tubing as defined in claim 29 which is essentially free of particulate silica.

35. A medical-surgical tubing as defined in claim 29 wherein said platinum-cured silicone network polymer (c) comprises the reaction product of
(i) an organic silicon compound having at least two silicon-bonded unsaturated groups per molecule,
(ii) a silicon compound containing at least two silicon-bonded hydrogen atoms per molecule, and
(iii) a small, catalytically effective amount of a platinum-containing catalyst.

36. A composition as defined in claim 35 wherein component (i) is of the formula:

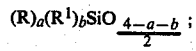

and component (ii) is of the formula:

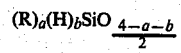

where R is selected from monovalent hydrocarbon radicals free of olefinic unsaturation, halogenated monovalent hydrocarbon radicals free of olefinic unsaturation, cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

37. A medical-surgical tubing as defined in claim 36 wherein said platinum-containing catalyst (iii) is selected from chloroplatinic acid, platinum black, platinum adsorbed on a carrier, a platinum-olefin complex, a platinum-cyclopropane complex or a mixture of any of the foregoing.

38. A medical-surgical tubing comprising:
(1) a relatively thick interior tubular portion which is visually transparent and transparent to x-ray radiation comprising:
   (a) a thermoplastic material; and
(2) a thin concentric outer shell which is visually transparent and strongly radiopaque comprising:
   (a) a thermoplastic material;
   (b) a radiopacifier which is an organic iodine compound; and
   (c) a platinum-cured silicone network polymer, the amount of (c) comprising 2 to 30 parts by weight per 100 parts by weight of (a), (b) and (c), said outer shell being co-extruded with and bonded to said interior portion, said outer shell having an external surface essentially free of exposed filler and rendered smooth and hard by extrusion.

39. A medical-surgical tubing as defined in claim 38 wherein component (a) of said inner and outer portions is a polyvinyl thermoplastic.

40. A medical-surgical tubing as defined in claim 38 wherein the tubing has a diameter of at least three-eights inch, and the outer shell has a wall thickness of 0.020 inch.

41. A medical-surgical tubing as defined in claim 38 wherein the inner tubular portion has relatively high flexibility and softness, said shell having greater hardness and torque resistance than said inner portion.

42. A medical-surgical tubing as defined in claim 38 wherein said radiopacifier (b) is of the formula:

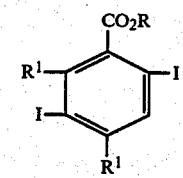

wherein $R^1$ is hydrogen or iodo, and R is alkyl or alkoxyalkyl or a mixture of said compounds.

43. A medical-surgical tubing as defined in claim 42 wherein, in said radiopacifier (b), each $R^1$ is iodo and R is (lower)alkyl or (lower)alkoxy(lower)alkyl.

44. A medical-surgical tubing as defined in claim 38 wherein said radiopacifier (b) is n-butyl 2,3,4,6-tetraiodobenzoate.

45. A medical-surgical tubing as defined in claim 38 wherein said radiopacifier (b) is 2-ethoxyethyl 2,5-diiodobenzoate.

46. A medical-surgical tubing as defined in claim 38 wherein said radiopacifier (b) comprises a mixture of n-butyl 2,3,4,6-tetraiodobenzoate and 2-ethoxyethyl 2,5-diiodobenzoate.

47. A medical-surgical tubing as defined in claim 38 which is essentially free of particulate silica.

48. A medical-surgical tubing as defined in claim 38 wherein said platinum-cured silicone network polymer (c) comprises the reaction product of
(i) an organic silicon compound having at least two silicon-bonded unsaturated groups per molecule,
(ii) a silicon compound containing at leat two silicon-bonded hydrogen atoms per molecule, and
(iii) a small, catalytically effective amount of a platinum-containing catalyst.

49. A medical-surgical tubing as defined in claim 48 wherein component (i) is of the formula:

$$(R)_a(R^1)_b\text{SiO}_{\frac{4-a-b}{2}};$$

and component (ii) is of the formula:

$$(R)_a(H)_b\text{SiO}_{\frac{4-a-b}{2}}$$

where R is selected from monovalent hydrocarbon radicals free of olefinic unsaturation, halogenated monovalent hydrocarbon radicals free of olefinic unsaturation, cyanoalkyl radicals or a mixture of any of the foregoing, $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

50. A medical-surgical tubing as defined in claim 49 wherein said platinum-containing catalyst (iii) is selected from chloroplatinic acid, platinum black, platinum adsorbed on a carrier, a platinum-olefin complex, a platinum-cyclopropane complex or a mixture of any of the foregoing.

51. A medical-surgical tubing comprising:
(1) an interior tubular portion comprising:
  (a) a vinyl resin which is a polymer or copolymer of a halogenated vinyl monomer;
  (b) a radiopacifier therefor consisting of a diiodobenzoate or a tetraiodobenzoate compound of the formula:

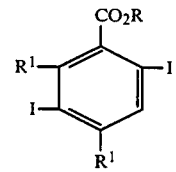

wherein
  $R^1$ is hydrogen or iodo;
  R is alkyl or alkoxyalkyl or a mixture of said compounds, said radiopacifier comprising 20 to 50 parts by weight per 100 parts by weight of (a) and (b); and, uniformly dispersed therein,
  (c) a platinum-cured, silicone network polymer, the amount of (c) comprising 2 to 30 parts by weight per 100 parts by weight of (a), (b) and (c); and
(2) a concentric outer shell comprising:
  (a) a thermoplastic polyurethane resin, wherein said medical-surgical tubing provides a surface essentially free of exposed filler.

* * * * *